(12) United States Patent
Holmberg et al.

(10) Patent No.: US 10,730,027 B2
(45) Date of Patent: Aug. 4, 2020

(54) APPARATUS AND PROCESS FOR THE PRODUCTION OF FORMALDEHYDE

(71) Applicant: JOHNSON MATTHEY PUBLIC LIMITED COMPANY, London (GB)

(72) Inventors: Johan Björn Mattias Holmberg, Perstorp (SE); Andreas Erik Johan Magnusson, Perstorp (SE)

(73) Assignee: Johnson Matthey Public Limited Company, London (GB)

( * ) Notice: Subject to any disclaimer, the term of this patent is extended or adjusted under 35 U.S.C. 154(b) by 173 days.

(21) Appl. No.: 15/775,167

(22) PCT Filed: Nov. 10, 2016

(86) PCT No.: PCT/GB2016/053509
§ 371 (c)(1),
(2) Date: May 10, 2018

(87) PCT Pub. No.: WO2017/081464
PCT Pub. Date: May 18, 2017

(65) Prior Publication Data
US 2020/0016560 A1 Jan. 16, 2020

(30) Foreign Application Priority Data

Nov. 13, 2015 (GB) .................................. 1520078.5
May 4, 2016 (GB) .................................. 1607783.6

(51) Int. Cl.
| | | |
|---|---|---|
| *C07C 45/00* | (2006.01) | |
| *B01J 8/00* | (2006.01) | |
| *B01J 8/04* | (2006.01) | |
| *B01J 8/06* | (2006.01) | |
| *C07C 47/04* | (2006.01) | |

(52) U.S. Cl.
CPC .............. *B01J 8/0496* (2013.01); *B01J 8/067* (2013.01); *C07C 45/002* (2013.01); *C07C 47/04* (2013.01); *B01J 2208/00212* (2013.01); *B01J 2208/00548* (2013.01)

(58) Field of Classification Search
CPC ........ C07C 45/002; B01J 8/067; B01J 8/0496
See application file for complete search history.

(56) References Cited

U.S. PATENT DOCUMENTS

| | | |
|---|---|---|
| 2,504,402 A | 4/1950 | Field |
| 4,343,954 A | 8/1982 | Hoene |
| 5,959,154 A | 9/1999 | Sioli |
| 5,986,146 A | 11/1999 | Sioli |
| 2015/0086437 A1 | 3/2015 | Matusz |

FOREIGN PATENT DOCUMENTS

| | | |
|---|---|---|
| EP | 1707259 A1 | 10/2006 |
| RU | 2561722 C1 | 9/2015 |
| WO | WO96/32189 A1 | 10/1996 |
| WO | WO 2007/111553 A1 | 10/2007 |
| WO | WO 2015/121611 A2 | 8/2015 |

OTHER PUBLICATIONS

PCT/GB2016/053509 International Search Report and Written Opinion dated Feb. 10, 2017.
GB1520078.5 Search Report Under Section 17(5) dated May 16, 2016.

*Primary Examiner* — Sikarl A Witherspoon
(74) *Attorney, Agent, or Firm* — BakerHostetler

(57) ABSTRACT

An apparatus for the production of formaldehyde is disclosed. The apparatus comprises a cooled tubular reactor section (8, 108, 208, 308, 408, 508) having a first inlet, a first outlet and a plurality of tubes each having a first end in fluid communication with the first inlet and a second end in fluid communication with the first outlet. The plurality of tubes contain a first catalyst for the production of formaldehyde by oxidative dehydrogenation. The apparatus is characterised in that the apparatus further comprises a pre-reactor section (7, 107, 207, 307, 407, 507). The pre-reactor section (7, 107, 207, 307, 407, 507) has an inlet. The pre-reactor section (7, 107, 207, 307, 407, 507) has an outlet in fluid communication with the first inlet of the cooled tubular reactor section (8, 108, 208, 308, 408, 508). The pre-reactor section (7, 107, 207, 307, 407, 507) is configured to contain, in use, an adiabatic catalyst bed. The adiabatic catalyst bed comprises a second catalyst for the production of formaldehyde by catalytic oxidative dehydrogenation.

20 Claims, 8 Drawing Sheets

APPARATUS AND PROCESS FOR THE PRODUCTION OF FORMALDEHYDE

CROSS-REFERENCE TO RELATED APPLICATIONS

This application is the National Stage of International Patent Application No. PCT/GB2016/053509, filed Nov. 10, 2016, which claims priority from Great Britain Patent Application No. 1520078.5, filed Nov. 13, 2015, and Great Britain Patent Application No. 1607783.6, filed May 4, 2016, the disclosures of each of which are incorporated herein by reference in their entireties for any and all purposes.

FIELD OF THE INVENTION

The present invention relates to an apparatus and process for the production of formaldehyde. More particularly, the invention relates to an apparatus and process for the production of formaldehyde by catalytic oxidative dehydrogenation using a mixed oxide catalyst such as an FeMo catalyst. More particularly, but not exclusively, the invention relates to an apparatus and process for the production of formaldehyde by catalytic oxidative dehydrogenation of methanol using a mixed oxide catalyst such as an FeMo catalyst.

BACKGROUND

Formaldehyde can be produced by the catalytic oxidative dehydrogenation of methanol. Processes for carrying out such production are known, for example from WO9632189 or U.S. Pat. No. 2,504,402. The catalyst typically comprises molybdenum and iron oxides. Formaldehyde can also be produced by a mix of catalytic oxidative dehydrogenation and catalytic dehydrogenation of methanol using a silver or copper catalyst. The present invention is concerned with the production of formaldehyde by catalytic oxidative dehydrogenation using mixed oxide catalysts. The reaction to form formaldehyde from methanol over mixed oxide catalysts is exothermic. The reaction may be carried out in an isothermal reactor, typically a tubular reactor, in which the heat of the reaction is removed by a heat transfer fluid. It will be understood that so-called "isothermal" reactors are typically pseudo isothermal in that the temperature varies along the length of the reactor despite the cooling provided to remove the heat of the reaction. Such reactors may also be termed "cooled" reactors. The reaction may also be carried out in an adiabatic reactor, in which heat is not removed and the temperature of the reactor contents increases as they pass through the reactor. Whichever reactor type is used, over time the catalyst ages, becomes less effective and needs replacing. Replacing the catalyst in a tubular reactor may take 4-5 days, during which time the reactor is shut down and revenue is being lost.

Most commercial plants today producing formaldehyde over mixed oxide catalysts are based on isothermal tubular reactors. The isothermal tubular reactor would typically be fed with up to 11 vol % methanol. Above that level a shortage of oxygen can lead to premature aging of the catalyst. The tubular reactors may be arranged in series, which can enable a higher methanol feed to be used than with a single reactor.

An adiabatic 'post-reactor' may also be added downstream of the isothermal tubular reactor. Such an adiabatic reactor is aimed at increasing the conversion of the methanol by compensating for inefficiency of the catalyst in the isothermal tubular reactor.

Preferred embodiments of the present invention seek to overcome one or more of the above disadvantages of the prior art. In particular, preferred embodiments of the present invention seek to provide an improved apparatus and process for the production of formaldehyde.

SUMMARY OF INVENTION

According to a first aspect of the invention, there is provided an apparatus for the production of formaldehyde, the apparatus comprising a cooled tubular reactor section having a first inlet, a first outlet and a plurality of tubes each having a first end in fluid communication with the first inlet and a second end in fluid communication with the first outlet, the plurality of tubes configured to contain, in use, a first catalyst for the production of formaldehyde by catalytic oxidative dehydrogenation, the apparatus being characterised in that the apparatus further comprises a pre-reactor section having an inlet and having an outlet in fluid communication with the first inlet of the cooled tubular reactor section, the pre-reactor section being configured to contain, in use, an adiabatic catalyst bed comprising a second catalyst for the production of formaldehyde by catalytic oxidative dehydrogenation.

Thus the invention provides an adiabatic pre-reactor section arranged upstream of the cooled tubular reactor section. The provision of an adiabatic pre-reactor section is advantageous in that it may be significantly faster to replace the catalyst in the pre-reactor section. The catalyst bed in the pre-reactor section is preferably a packed bed of catalyst, which can be removed and replaced in a few hours. That is very much quicker than the 4-5 day replacement time of the catalyst in the tubes of the tubular reactor. The upstream catalyst ages more quickly. In prior tubular reactors, the aging of the catalyst near the start of the tubes dominated the catalyst replacement cycle requirements. In the present invention, the catalyst in the pre-reactor section can be changed more often, with a short replacement time, and the catalyst in the tubular reactor section can be replaced at longer intervals. The result is that long shut down periods to replace the catalyst in the tubes are only needed at much wider time intervals. The presence of the pre-reactor section may also reduce the heat load on the cooled tubular reactor section (i.e. the heat generated by the reaction in the cooled tubular reactor section, which needs to be removed on the shell side of the cooled tubular reactor section). Thus the invention advantageously permits existing plants with cooled tubular reactor sections with short tubes to be upgraded to increase capacity. The invention also advantageously allows better temperature control in the cooled tubular reactor section. In prior art reactors, the heat transfer fluid temperature needed to account for the high levels of heat resulting from the high reaction rate in the early part of the tubes. However, with a pre-reactor section present, the initial reaction rate in the cooled tubular reactor section can be lower and the heat transfer fluid can be better adjusted to the heat generation along the entire length of the tube. The invention also advantageously increases average yields over an extended period of time, for example on a yearly basis, because of the ability to replace the catalyst in the pre-reactor section more frequently. In the past, the length of time required for a catalyst load may have led to a balance between decreasing yield and the cost of a shut down. In the present invention, the catalyst in the cooled tubular reactor section lasts for a longer time, and the catalyst in the pre-reactor section can be kept refreshed by more frequent changes that are more rapidly accomplished. As a result, the overall aging of the catalyst is reduced and the average yield over an extended period of time is increased. Preferably the invention permits average yield increases of up to 0.5% over prior art systems and up to 2% immediately after re-loading the catalyst in the adiabatic pre-reactor section compared to prior art systems without a re-load at that point.

The cooled tubular reactor section is preferably a heat transfer fluid cooled tubular reactor section. Preferably the cooled tubular reactor section further comprises a shell surrounding the plurality of tubes and having at least one second inlet and at least one second outlet for passing heat transfer fluid through the shell in use. Thus the cooled tubular reactor section may be a tubular reactor section having a first inlet, a first outlet and a plurality of tubes each having a first end in fluid communication with the first inlet and a second end in fluid communication with the first outlet, the plurality of tubes configured to contain, in use, a first catalyst for the production of formaldehyde by catalytic oxidative dehydrogenation, the cooled tubular reactor section further comprising a shell surrounding the tubes and configured to contain a heat transfer medium, for example a heat transfer fluid. The cooled tubular reactor section may be configured such that, in use, the heat transfer medium removes heat generated in the tubes. For example, the shell may have at least one second inlet and at least one second outlet for passing heat transfer fluid through the shell in use. Preferably the tubes contain the first catalyst.

The pre-reactor section is configured to contain, in use, an adiabatic catalyst bed. Preferably the pre-reactor section comprises the adiabatic catalyst bed. Preferably the catalyst bed is a packed bed comprising the second catalyst. Preferably the catalyst bed is a single bed. That is, the catalyst bed is not a tubular arrangement but instead is a packed bed of catalyst extending across the flow path. In some embodiments that catalyst bed may comprise a small number, for example 2 or 3 or 4 beds in parallel. However, the catalyst bed is not a tubular bed and there is not provision for heat removal from within the catalyst bed. Thus the catalyst bed is said to be an adiabatic catalyst bed. It will be appreciated that the speed of replacement of the catalyst bed compared to a tubular bed is important. Thus the catalyst bed may be arranged such that it can be replaced in no more than 4, preferably 3 and more preferably 2 hours. That may be achieved by having a single packed bed or a small number, for example, 2 or 3 or 4, of beds in parallel.

The second catalyst may be the same as the first catalyst, or it may be different from the first catalyst. Either or both of the first or second catalysts may comprise a mixture, or structured arrangement, such as layers, of one or more catalysts. That may be advantageous in providing different catalysts at different parts of the reactors to optimise performance. Thus the first catalyst may be a single catalyst or it may be a mixture of catalysts. The second catalyst may be a single catalyst or a mixture of catalysts. The first or second catalyst may be mixed with non-active components such as ceramic rings. The first and second catalysts are catalysts for the production of formaldehyde by catalytic oxidative dehydrogenation. Preferably either or both of the catalysts are catalysts for the production of formaldehyde by catalytic oxidative dehydrogenation of methanol. Preferably the catalysts are mixed oxide catalysts, for example FeMo catalysts.

Preferably the cross-sectional area (i.e. the area perpendicular to the general flow direction) of the catalyst bed of the pre-reactor section is substantially the same as the tubular cross-sectional area of the cooled tubular reactor section (i.e. the sum of the cross-sectional areas of the tubes). For example the cross-sectional area of the catalyst bed of the pre-reactor section may be in the range of 50% to 150%, and preferably 70% to 130%, of the tubular cross-sectional area of the cooled tubular reactor section. In some embodiments the apparatus may comprise a plurality of cooled tubular reactor sections arranged in parallel with the outlet of the pre-reactor section being in communication with the first inlet of each of the cooled tubular reactor sections. In such embodiments, the tubular cross-sectional area of the cooled tubular reactor sections will be understood as being the sum of the cross sectional areas of each cooled tubular reactor section (i.e. the sum of the cross-sectional areas of the tubes in all the parallel tubular reactor sections).

In some embodiments the pre-reactor section and the cooled tubular reactor section may be housed in series in a single vessel. Cooling apparatus, such as cooling coils, may be arranged between the sections. Preferably the pre-reactor section is in a separate vessel to the cooled tubular reactor section. Thus the apparatus may comprise a pre-reactor containing the pre-reactor section and a cooled tubular reactor containing the cooled tubular reactor section. Preferably the apparatus includes a bypass across the pre-reactor. In that way the apparatus can be operated with the pre-reactor isolated while the catalyst in the pre-reactor is replenished, thus further increasing the productivity of the apparatus.

Preferably the apparatus includes a heat exchanger connected to the inlet and the outlet of the pre-reactor such that, in use, the gas leaving the pre-reactor is used to heat the feed to the pre-reactor. Advantageously, that cools the gas before it is passed to the cooled tubular reactor and heats the feed to the desired temperature at the inlet to the pre-reactor. Preferably the apparatus further comprises a bypass valve connected between an input and an output of the heat exchanger such that some or all of a stream exiting the pre-reactor can be diverted so as to bypass the heat exchanger. Such a bypass valve may advantageously allow control of the temperature of the stream passed to the inlet of the pre-reactor. The apparatus of the invention advantageously allows the temperature of the pre-reactor to be controlled by adjusting the inlet temperature to that reactor. Thus the temperature in the pre-reactor may be different from the temperature in the tubular reactor, allowing further options for optimising the process. The ability to control the temperature of the pre-reactor by adjusting the temperature at the inlet and the to reduce the temperature of the gases between the outlet of the pre-reactor and the inlet of the cooled tubular reactor permits the process to run more efficiently, for example by adjusting the conditions as the catalyst ages.

Preferably the apparatus comprises a steam generator connected to the outlet of the pre-reactor section to generate steam and cool the gases leaving the pre-reactor section. That may advantageously provide cooler gases for feeding to the cooled tubular reactor section and produce useful steam while doing so. In some embodiments, the steam generator may be connected to an output of the heat exchanger, so that a stream exiting the pre-reactor section flows in use to the steam generator via the heat exchanger. In some embodiments the steam generator may be connected directly (i.e. without an intervening unit operation) to the output of the pre-reactor section. In such embodiments an output of the steam generator may be connected to the heat exchanger, so that a stream exiting the pre-reactor flows in use to the heat exchanger via the steam generator. Alternatively in such embodiments, the output of the steam generator may be connected directly to the first inlet of the cooled tubular reactor section.

Preferably the apparatus comprises a further feed inlet connected to the first inlet of the cooled tubular reactor section. For example the further feed inlet may take the form of a valve into a pipe carrying the stream from the pre-reactor section to the cooled tubular reactor section. The further feed inlet may be used to add further methanol to the stream of gases exiting the pre-reactor section before they are fed to the cooled tubular reactor section. That may be advantageous in allowing extra methanol to be added to the process, thus increasing the formaldehyde product flow leaving the cooled tubular reactor section.

In some embodiments the apparatus may be provided with a heat exchanger connected to the first input and the first output of the cooled tubular reactor section such that heat can be exchanged between streams flowing to and from the cooled tubular reactor section. Such arrangements may make advantageous use of heat in the stream leaving the cooled tubular reactor section. In such embodiments the further feed inlet may be a further feed inlet into the heat exchanger. That may be advantageous in that heat from the stream leaving the cooled tubular reactor section may be used to assist in vaporisation of the methanol added through the further feed inlet.

Advantageously the apparatus is provided with a turbocharger to pressurise gas entering the apparatus. The gas is pressurised before it is fed to the pre-reactor section. Thus the turbocharger is upstream of the pre-reactor section. Preferably the turbocharger is powered by energy from the waste gas from the production of the formaldehyde. For example, in some embodiments waste gases from the production may be combusted, for example in an emissions control system, and the energy used to power the turbocharger. For example, in some embodiments the volume flow through the apparatus, which is increased by the exothermic nature of the formaldehyde production and/or the waste gas combustion, may be used to power the turbocharger. For example, the apparatus may comprise an absorber, or other formaldehyde recovery unit, downstream of the cooled tubular reactor section, and downstream of optional heat exchangers or steam generators, and an emissions control system downstream of the absorber. The gases exiting the cooled tubular reactor section may pass to the absorber to recover the formaldehyde, with the remaining gas exiting the absorber (for example, the waste gas) being passed to the emissions control system. In the emissions control system, the waste gas is preferably burnt, for example by catalytic incineration, to remove hazardous components. The hot gas exiting the emissions control system may be passed to a turbine side of the turbocharger to power the compression of gases entering the apparatus on a compressor side of the turbocharger. The turbine may power the compressor directly, for example via an axle, or it may power the compressor indirectly, for example by powering a generator, which in turn provides electrical power to the compressor. The turbine velocity may be regulated by means of a throttle valve and/or a bypass stream. A suitable turbocharger system may be as described in WO2007111553. The use of such a turbocharger system is particularly advantageous with a pre-reactor section as it permits the pre-reactor section to be run at high pressure without incurring excessive compression costs. That gives particular benefits in a system according to the present invention in which a pre-reactor section is present because the increased pressure increases throughput and hence production of formaldehyde. In previous systems that advantage would need to be weighed against the decreased catalyst lifetime and the resulting increase in frequency of shuts down for catalyst changes. However, in the present invention, the greatest degradation of catalyst occurs in the pre-reactor section, where the catalyst can be more straightforwardly changed. Thus the advantages of high pressure operation can be realised without the previous accompanying drawbacks.

According to a second aspect of the invention there is provided a process for producing formaldehyde, the process comprising feeding a feed stream comprising methanol to a pre-reactor section operated adiabatically, at least partially converting methanol in the feed stream to formaldehyde in the pre-reactor section to produce a first product stream comprising formaldehyde, feeding the first product stream to a cooled tubular reactor section, and at least partially converting methanol in the first product stream to formaldehyde in the cooled tubular reactor section to produce a second product stream comprising formaldehyde. Optionally further methanol can be added to the first product stream, for example by combining the first product stream with a further methanol containing stream, prior to feeding the first product stream to the cooled tubular reactor section.

The pre-reactor section may be operated adiabatically in that there is no provision made for heat removal from that section.

Preferably not less than 10% and not more than 100%, in some embodiments not more than 95%, of the methanol in the feed stream is converted to formaldehyde in the pre-reactor section. If no extra methanol is added to the first product stream before it is fed to the cooled tubular reactor section then preferably not more than 40% of the methanol in the feed stream is converted to formaldehyde in the pre-reactor section. Such a conversion range advantageously provides the benefits of carrying out the initial reaction in a pre-reactor section whose catalyst can be more easily changed whilst retaining the heat removal benefits, and the ability to control heat removal in response to catalyst aging, of the cooled tubular reactor section.

The process may comprise adding methanol to the first product stream before feeding it to the cooled tubular reactor. That may increase the formaldehyde productivity of the process. For example up to 30% more methanol may be fed to the process across the two feed locations than would be possible in a prior art system with a single feed.

In some embodiments, all of the methanol may be added in the feed stream. That is, in such embodiments, no methanol is added to the first product stream. Such embodiments may be particularly advantageous where there is a risk of contaminants in the methanol that might lead to poisoning of the catalyst. The poisons will typically affect the first catalyst they come to. In prior art systems, that catalyst was in tubes and was therefore difficult and costly to replace. In the present invention the catalyst most likely to be poisoned is the catalyst in the pre-reactor section, which is more straightforward to replace.

Preferably the cooled tubular reactor section comprises a plurality of tubes containing a first catalyst for the oxidative dehydrogenation of methanol to formaldehyde and the process comprises passing the first product stream through the tubes to at least partially convert methanol in the first product stream to formaldehyde. Preferably the cooled tubular reactor section further comprises a shell surrounding the plurality of tubes and the process comprises removing heat from the tubes using a heat transfer medium, for example a heat transfer fluid, in the shell. For example, the process preferably comprises passing a heat transfer fluid through the shell to remove heat from the tubes. Thus the cooled tubular reactor section may be a tubular reactor section having a plurality of tubes containing a first catalyst for the oxidative dehydrogenation of methanol to formaldehyde, the tubular reactor section further comprising a shell surrounding the tubes and containing a heat transfer medium, for example a heat transfer fluid.

Preferably the pre-reactor section comprises a catalyst bed and the process comprises passing the feed stream through the catalyst bed to at least partially convert methanol in the feed stream to formaldehyde. Preferably the catalyst bed contains a second catalyst for the oxidative dehydrogenation of methanol to formaldehyde. Preferably the catalyst bed is a packed bed comprising the second catalyst.

The second catalyst may be the same as the first catalyst, or it may be different from the first catalyst. Either or both of the first or second catalysts may comprise a mixture, or structured arrangement, such as layers, of one or more catalysts. That may be advantageous in providing different catalysts at different parts of the reactors to optimise performance. Thus the first catalyst may be a single catalyst or it may be a mixture of catalysts. The second catalyst may be a single catalyst or a mixture of catalysts. Preferably the first and second catalysts are mixed oxide catalysts, such as FeMo catalysts.

Preferably the catalyst in the pre-reactor section is changed more often than the catalyst in the cooled tubular reactor section. For example, the catalyst in the pre-reactor section may be changed from 1 to 5 times, preferably from 2 to 5 times and yet more preferably from 2 to 3 times, per change of the catalyst in the cooled tubular reactor section. Preferably the process comprises operating the process for a period of time, and replacing the catalyst in the pre-reactor section one or more times with a fresh catalyst bed during the period of time, wherein the catalyst in the cooled tubular reactor section is not replaced during the period of time. Preferably the process comprises operating the process, operating a bypass so that the pre-reactor section is isolated from the process and the feed stream is fed to the cooled tubular reactor section, replacing the catalyst in the pre-reactor section, and reversing the operation of the bypass so that the feed stream is once more fed to the pre-reactor section. The pre-reactor section is thus removed from the process to replace the catalyst and then returned to the process after the catalyst is replaced. The period of time may for example be a month, or 3 months or preferably 6 months.

Preferably the process comprises feeding waste gas from the process to a turbocharger and using energy in the waste gas to compress feed gas to the process via the turbocharger. Preferably the feed gas is fresh air. The feed stream comprising methanol is preferably created by mixing methanol with the compressed feed gas after the feed gas is mixed with recycled oxygen lean gas leaving the process. Thus the turbocharger operates to pressurise the feed stream comprising methanol, since the pressurising of the feed gas raises the resulting pressure of the feed stream comprising methanol. The turbocharger also operates to introduce oxygen to the process by the introduction of the fresh air. The turbocharger is preferably operated to control the oxygen level and pressure of the feed stream. Preferably the waste gas is fed to an emissions control system, where hazardous substances are removed by combustion, before being passed to the turbocharger.

It will be appreciated that features described in relation to one aspect of the invention may be equally applicable in another aspect of the invention. For example, features described in relation to the apparatus of the invention, may be equally applicable to the process of the invention, and vice versa. Some features may not be applicable to, and may be excluded from, particular aspects of the invention.

DESCRIPTION OF THE DRAWINGS

Embodiments of the present invention will now be described, by way of example, and not in any limitative sense, with reference to the accompanying drawings, of which.

DETAILED DESCRIPTION

Figure 1:
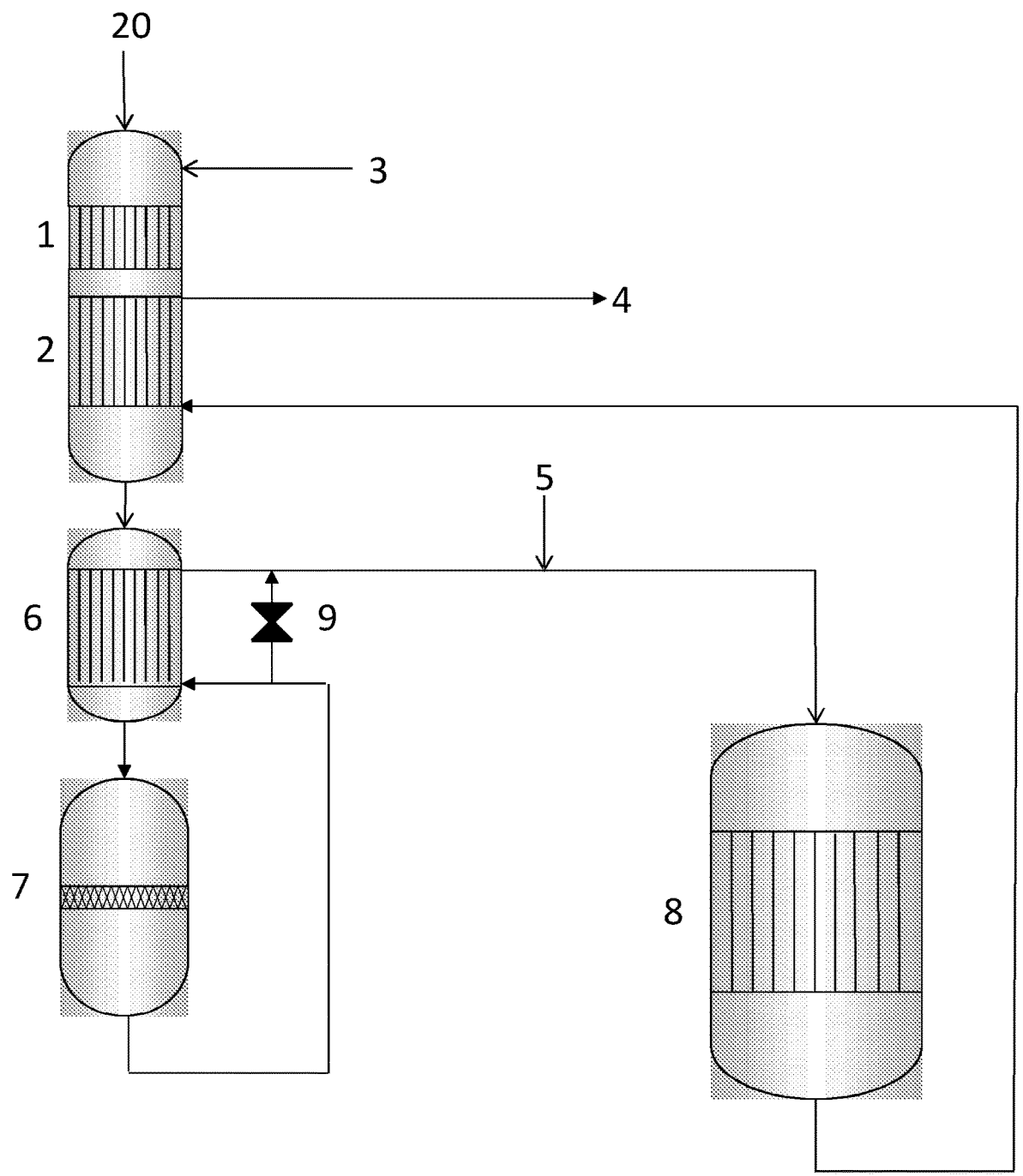
FIG. 1 is a schematic diagram of an embodiment of the present invention.

In FIG. 1 a pre-vaporiser 1 is fed with a feed stream 3 comprising methanol and a recirculation stream 20. The feed stream 3 and the recirculation stream 20 are mixed and passed through the pre-vaporiser 1 and a vaporiser 2, which together vaporise and heat the mixture. The vaporised stream is passed to a pre-heater 6 and then to a pre-reactor 7. In the pre-reactor 7 at least some of the methanol is converted to formaldehyde in a single adiabatically operated catalyst bed. The stream leaving the pre-reactor 7 passes through pre-heater 6 and on to a cooled tubular reactor 8. In the pre-heater 6 heat is exchanged between the output and input streams of the pre-reactor 7 thus cooling the output and heating the input. A bypass valve 9 permits control of the temperature of the stream entering the pre-reactor 7. Extra methanol 5 can be added to the stream entering the cooled tubular reactor 8. In the cooled tubular reactor 8, methanol remaining from the pre-reactor 7 or added by the methanol addition 5 is converted to formaldehyde. The product stream from the tubular reactor 8 passes through the vaporiser 2, where heat from the product stream is used to vaporise and heat the mixture of feed stream 3 and recirculation stream 20, and then on to an absorber 4 to recover the formaldehyde from the product stream. Recycled gas from the absorber is mixed with fresh air to form recirculation stream 20. The recycle improves the yield and reduces the concentration of oxygen, which reduces the explosion risk.

Figure 2:
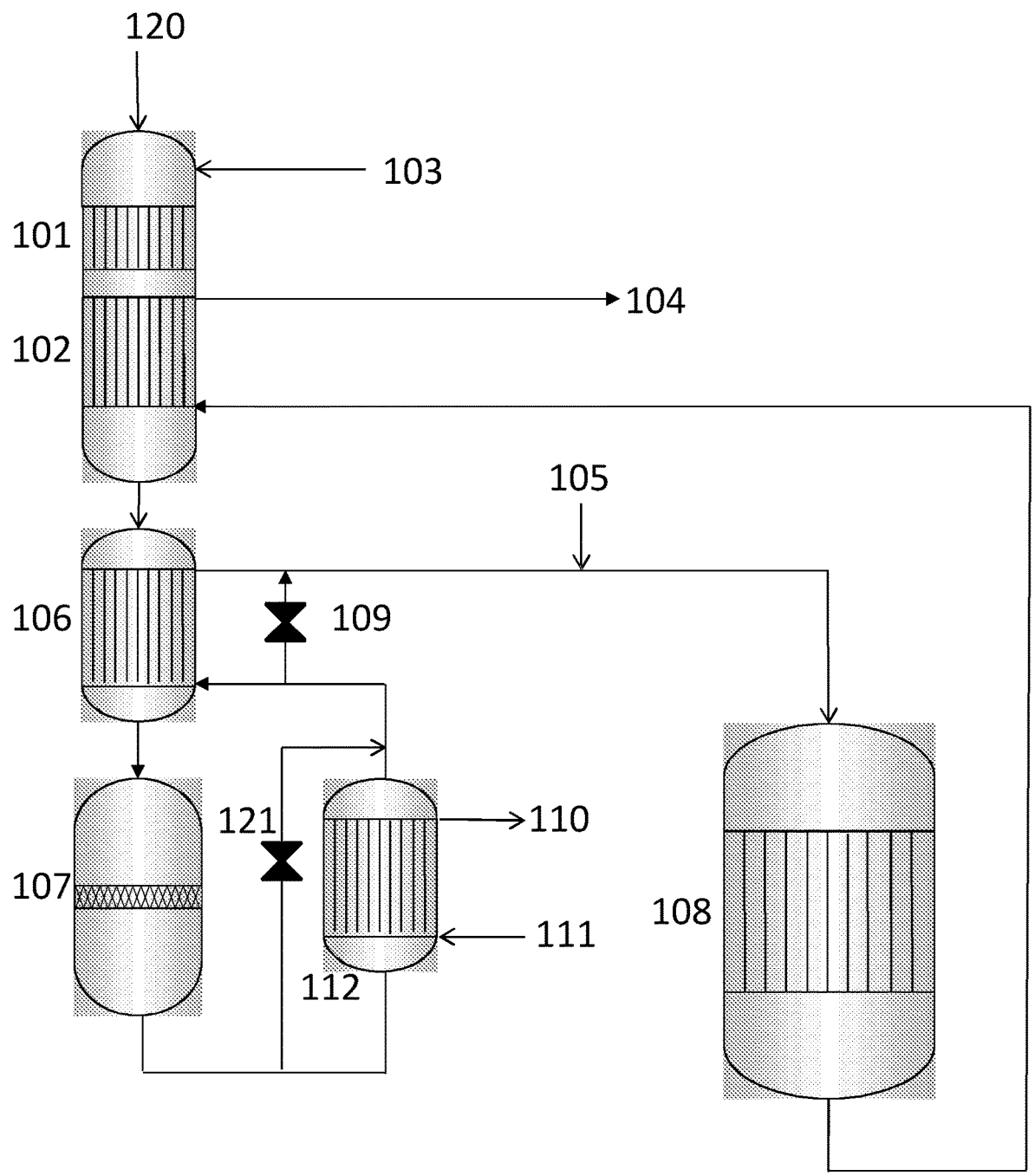
FIG. 2 is a schematic diagram of another embodiment of the present invention.

In FIG. 2 a pre-vaporiser 101 is fed with a feed stream 103 comprising methanol and a recirculation stream 120. The feed stream 103 and the recirculation stream 120 are mixed and passed through the pre-vaporiser 101 and a vaporiser 102, which together vaporise and heat the mixture. The vaporised stream is passed to a pre-heater 106 and then to a pre-reactor 107. In the pre-reactor 107 at least some of the methanol is converted to formaldehyde in a single adiabatically operated packed bed of catalyst. The stream leaving the pre-reactor 107 passes through a steam generator 112, where heat from the stream is exchanged with boiler feed water 111 to produce steam 110. A bypass valve 121 is provided across the steam generator 112. The stream then passes through pre-heater 106 and on to a cooled tubular reactor 108. In the pre-heater 106 heat is exchanged between the output and input streams of the pre-reactor 107 thus cooling the output and heating the input. A bypass valve 109 permits control of the temperature of the stream entering the pre-reactor 107. Extra methanol 105 can be added to the stream entering the cooled tubular reactor 108. In the tubular reactor 108, methanol remaining from the pre-reactor 107 or added by the methanol addition 105 is converted to formaldehyde. The product stream from the cooled tubular reactor 108 passes through the vaporiser 102, where heat from the product stream is used to vaporise and heat the mixture of feed stream 103 and recirculation stream 120, and then on to an absorber 104 to recover the formaldehyde from the product stream. Recycled gas from the absorber is mixed with fresh air to form recirculation stream 120.

Figure 3:
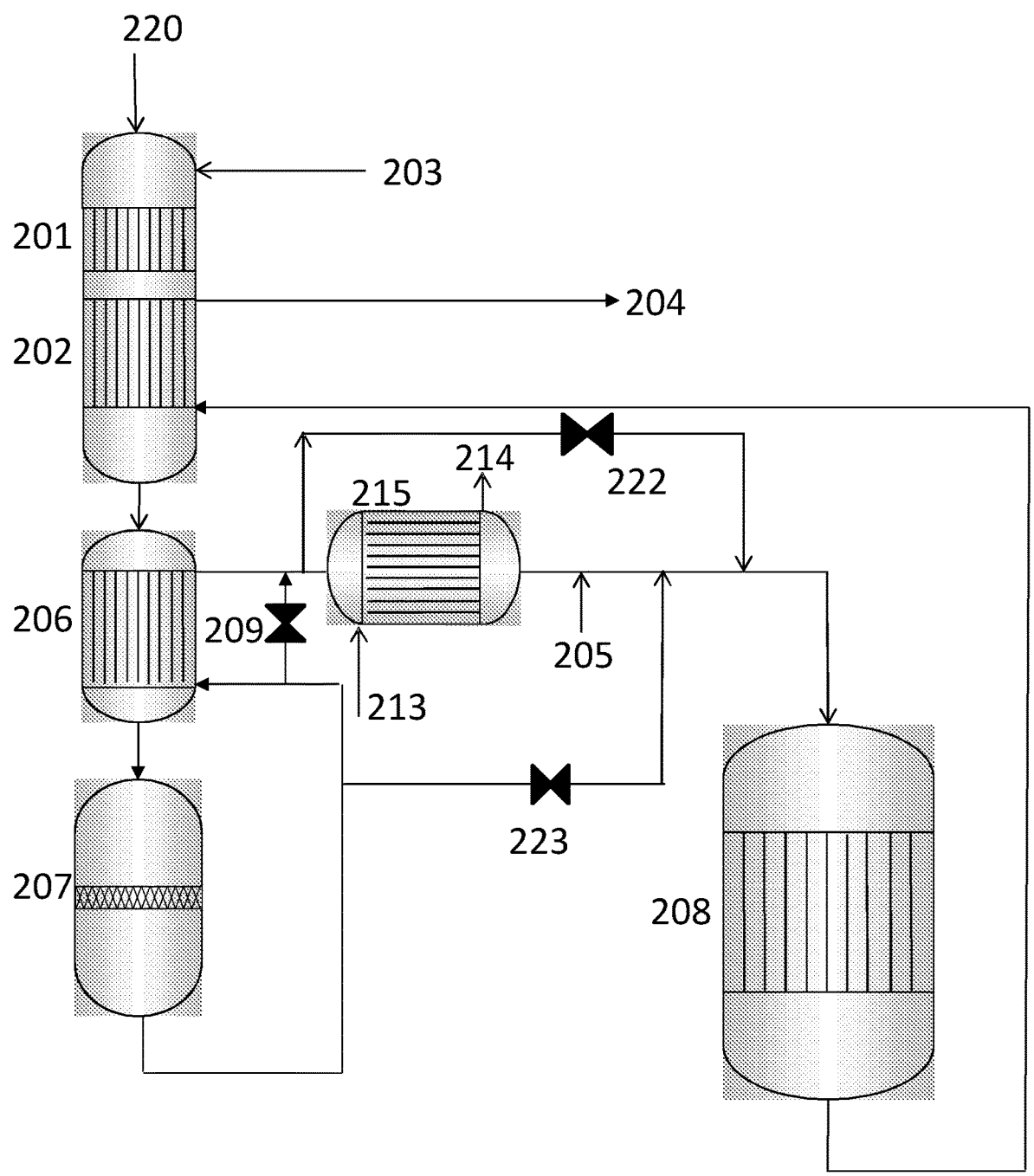
FIG. 3 is a schematic diagram of another embodiment of the present invention.

In FIG. 3 a pre-vaporiser 201 is fed with a feed stream 203 comprising methanol and a recirculation stream 220. The feed stream 203 and the recirculation stream 220 are mixed and passed through the pre-vaporiser 201 and a vaporiser 202, which together vaporise and heat the mixture. The vaporised stream is passed to a pre-heater 206 and then to a pre-reactor 207. In the pre-reactor 207 at least some of the methanol is converted to formaldehyde in a single adiabatically operated catalyst bed. The stream leaving the pre-reactor 207 passes through pre-heater 206 where heat is exchanged between the output and input streams of the pre-reactor 207 thus cooling the output and heating the input. A bypass valve 209 permits control of the temperature of the stream entering the pre-reactor 207. The stream exiting the pre-heater 206 passes on to a steam generator 215, where heat from the stream is exchanged with boiler feed water 213 to produce steam 214. Bypass valves 222 and 223 are provided across the steam generator 215 and across the pre-heater 206 and steam generator 215. The stream then passes on to a cooled tubular reactor 208. Extra methanol 205 can be added to the stream entering the cooled tubular reactor 208. In the cooled tubular reactor 208, methanol remaining from the pre-reactor 207 or added by the methanol addition 205 is converted to formaldehyde. The product stream from the cooled tubular reactor 208 passes through the vaporiser 202, where heat from the product stream is used to vaporise and heat the mixture of feed stream 203 and recirculation stream 220, and then on to an absorber 204 to recover the formaldehyde from the product stream. Recycled gas from the absorber is mixed with fresh air to form recirculation stream 220.

Figure 4:
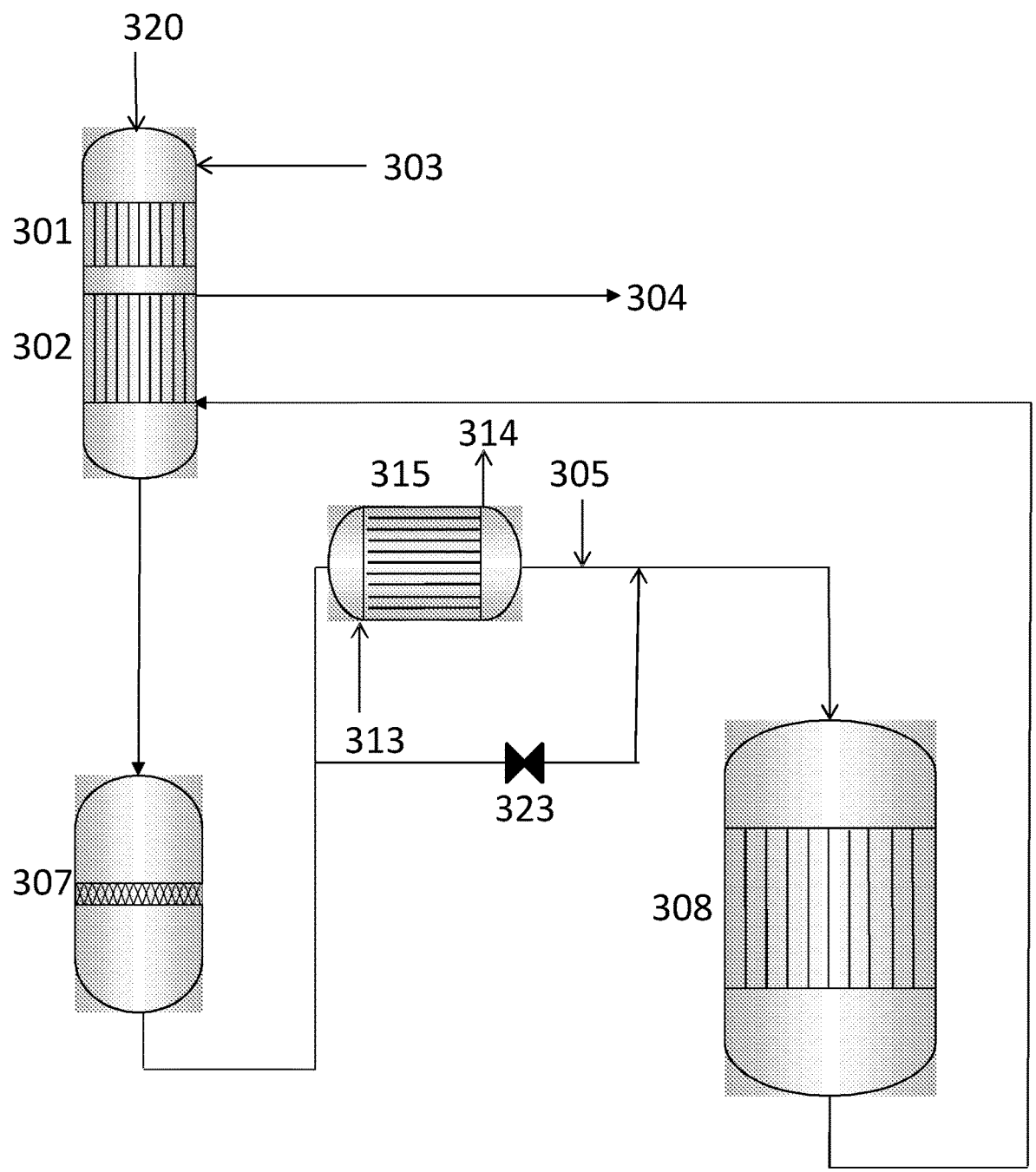
FIG. 4 is a schematic diagram of another embodiment of the present invention.

In FIG. 4 a pre-vaporiser 301 is fed with a feed stream 303 comprising methanol and a recirculation stream 320. The feed stream 303 and the recirculation stream 320 are mixed and passed through the pre-vaporiser 301 and a vaporiser 302, which together vaporise and heat the mixture. The vaporised stream is passed to a pre-reactor 307. In the pre-reactor 307 at least some of the methanol is converted to formaldehyde in a single adiabatically operated catalyst bed. The stream leaving the pre-reactor 307 passes to a steam generator 315, where heat from the stream is exchanged with boiler feed water 313 to produce steam 314. There is a bypass valve 323 across the steam generator 315. The stream then passes on to a cooled tubular reactor 308. Extra methanol 305 can be added to the stream entering the cooled tubular reactor 308. In the cooled tubular reactor 308, methanol remaining from the pre-reactor 307 or added by the methanol addition 305 is converted to formaldehyde. The product stream from the cooled tubular reactor 308 passes through the vaporiser 302, where heat from the product stream is used to vaporise and heat the mixture of feed stream 303 and recirculation stream 320, and then on to an absorber 304 to recover the formaldehyde from the product stream. Recycled gas from the absorber is mixed with fresh air to form recirculation stream 320.

Figure 5:
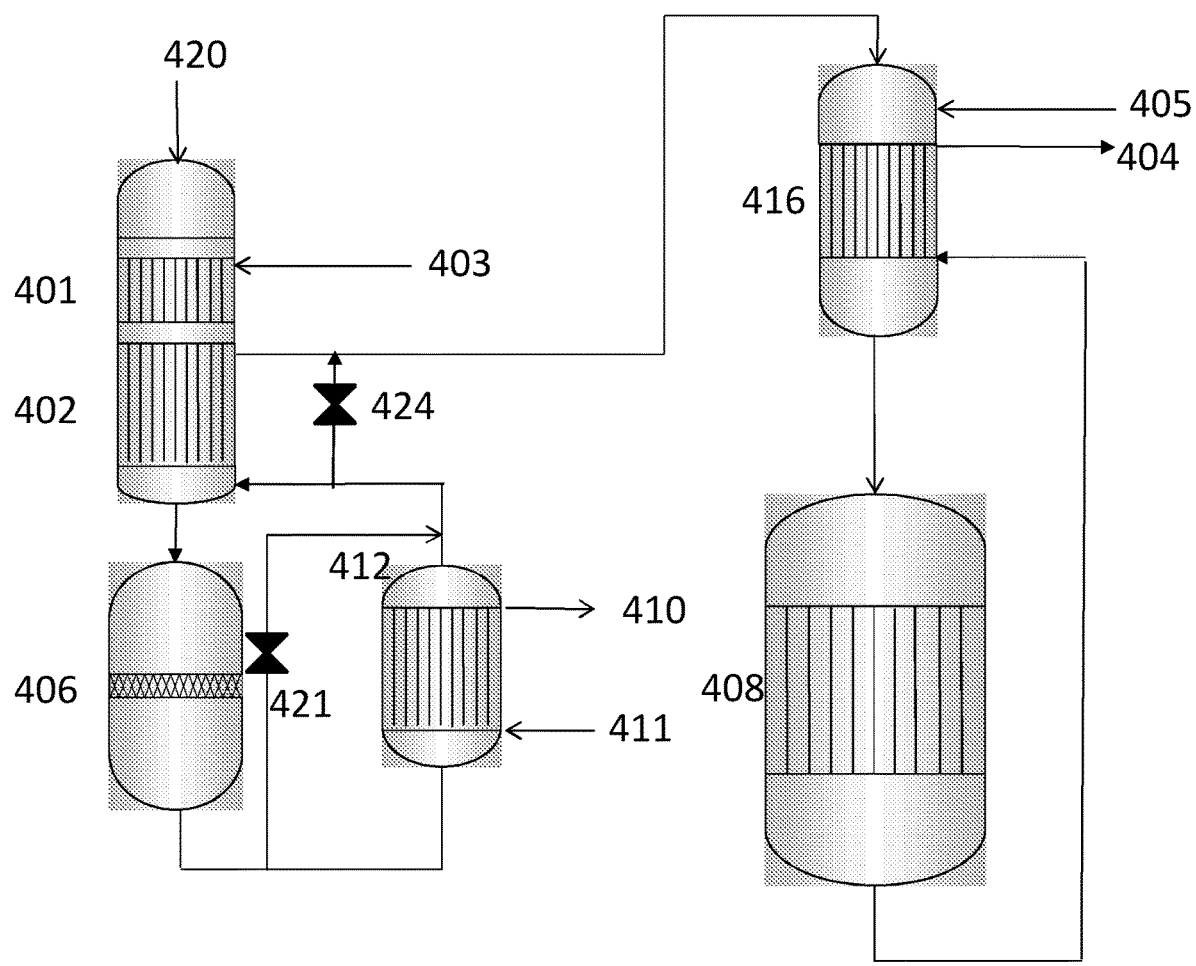
FIG. 5 is a schematic diagram of another embodiment of the present invention.

In FIG. 5 a pre-vaporiser 401 is fed with a feed stream 403 comprising methanol and a recirculation stream 420. The feed stream 403 and the recirculation stream 420 are mixed and passed through the pre-vaporiser 401 and vaporiser 402, which together vaporise and heat the mixture. The vaporised stream is passed to a pre-reactor 407. In the pre-reactor 407 at least some of the methanol is converted to formaldehyde in a single adiabatically operated catalyst bed. The stream leaving the pre-reactor 407 passes through a steam generator 412, where heat from the stream is exchanged with boiler feed water 411 to produce steam 410. The stream then passes through pre-heater 402, where heat is exchanged with the feed stream 403, and on to a vaporiser and gas cooler 416. There is a bypass valve 421 across the steam generator 412 and a bypass valve 424 across the pre-heater 402. Extra methanol 405 can be added to the stream in the vaporiser and gas cooler 416 and the combined stream fed to a cooled tubular reactor 408. In the cooled tubular reactor 408, methanol remaining from the pre-reactor 407 or added by the methanol addition 405 is converted to formaldehyde. The product stream from the cooled tubular reactor 408 passes through the vaporiser and gas cooler 416, where heat from the product stream is exchanged with the stream flowing to the cooled tubular reactor 408, and then on to an absorber 404 to recover the formaldehyde from the product stream. Recycled gas from the absorber is mixed with fresh air to form recirculation stream 420.

Figure 6:
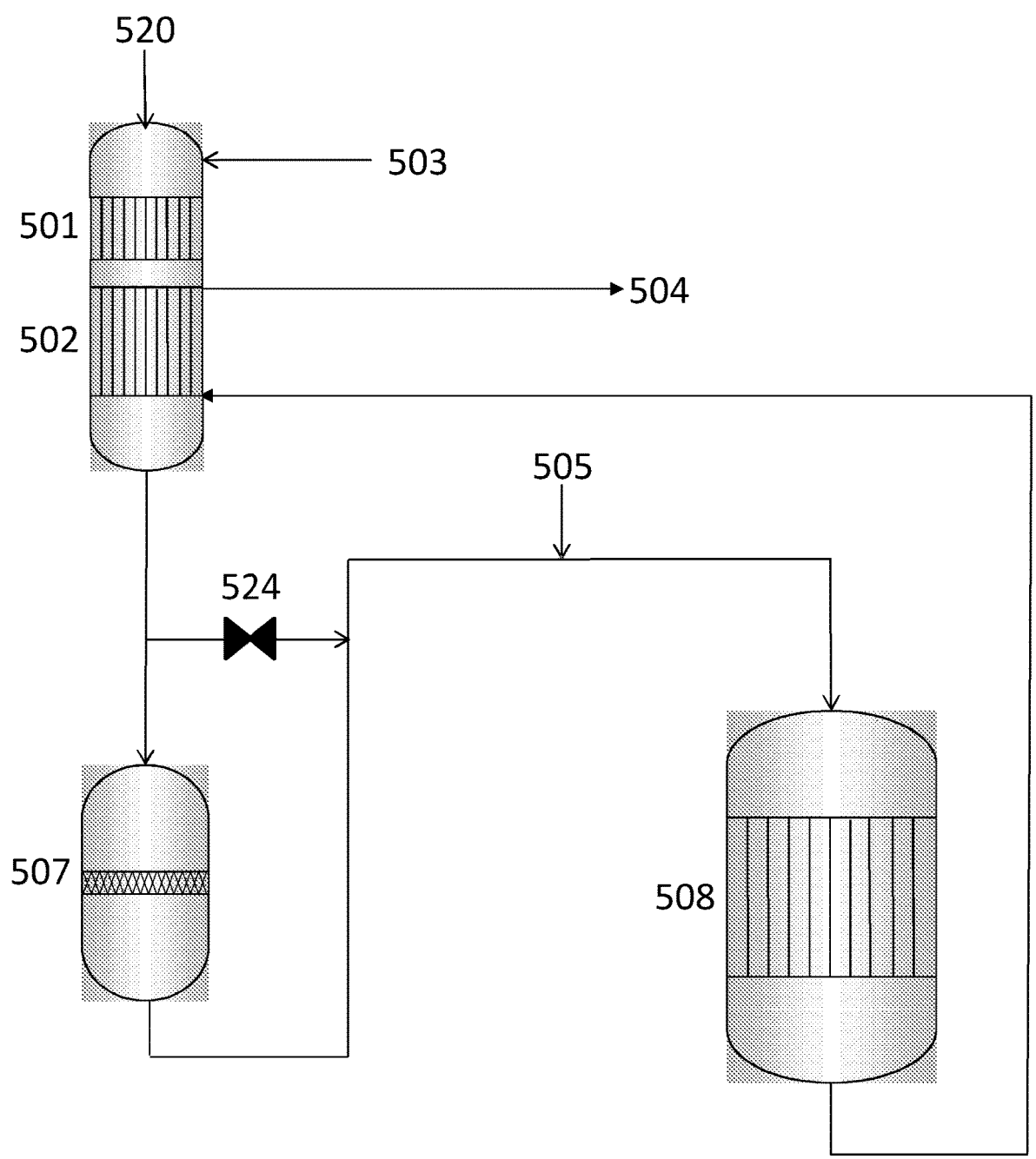
FIG. 6 is a schematic diagram of another embodiment of the present invention.

In FIG. 6 a pre-vaporiser 501 is fed with a feed stream 503 comprising methanol and a recirculation stream 520. The feed stream 503 and the recirculation stream 520 are mixed and passed through the pre-vaporiser 501 and a vaporiser 502, which together vaporise and heat the mixture. The vaporised stream is passed to a pre-reactor 507. In the pre-reactor 507 at least some of the methanol is converted to formaldehyde in a single adiabatically operated catalyst bed. The stream leaving the pre-reactor 507 passes to a cooled tubular reactor 508. Extra methanol 505 can be added to the stream entering the cooled tubular reactor 508. In the cooled tubular reactor 508, methanol remaining from the pre-reactor 507 or added by the methanol addition 505 is converted to formaldehyde. The product stream from the tubular reactor 508 passes through the vaporiser 502, where heat from the product stream is used to vaporise and heat the mixture of feed stream 503 and recirculation stream 520, and then on to an absorber 504 to recover the formaldehyde from the product stream. Recycled gas from the absorber is mixed with fresh air to form recirculation stream 520. In this embodiment a bypass 524 allows the pre-reactor 507 to be isolated from the process so that the catalyst in the pre-reactor 507 can be changed while the process continues to operate with the feed being directed to the cooled tubular reactor 508. Such a bypass 524 could also be included on the embodiments illustrated in the other figures.

Figure 7:
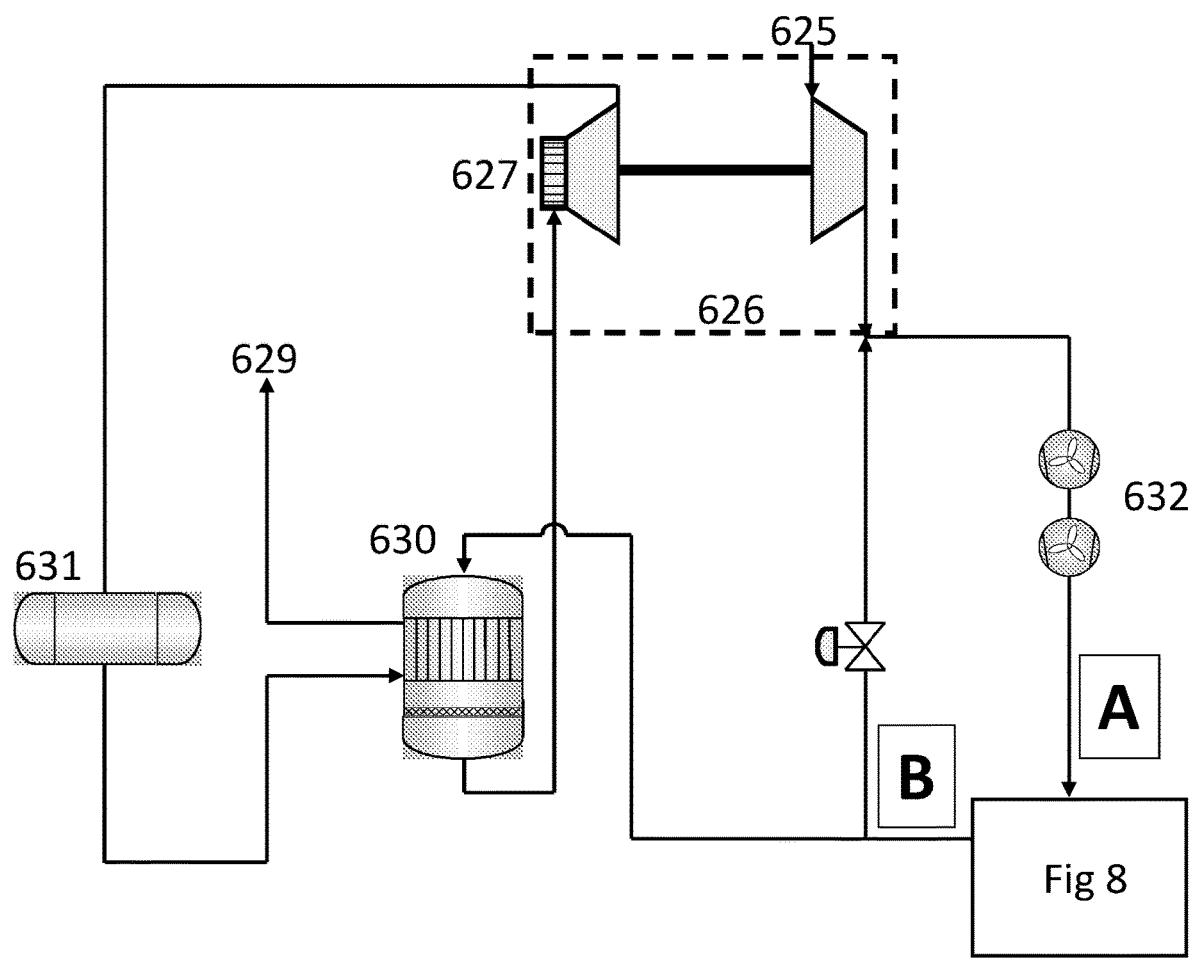
FIG. 7 is a schematic diagram of part of another embodiment of the present invention.
Figure 8:
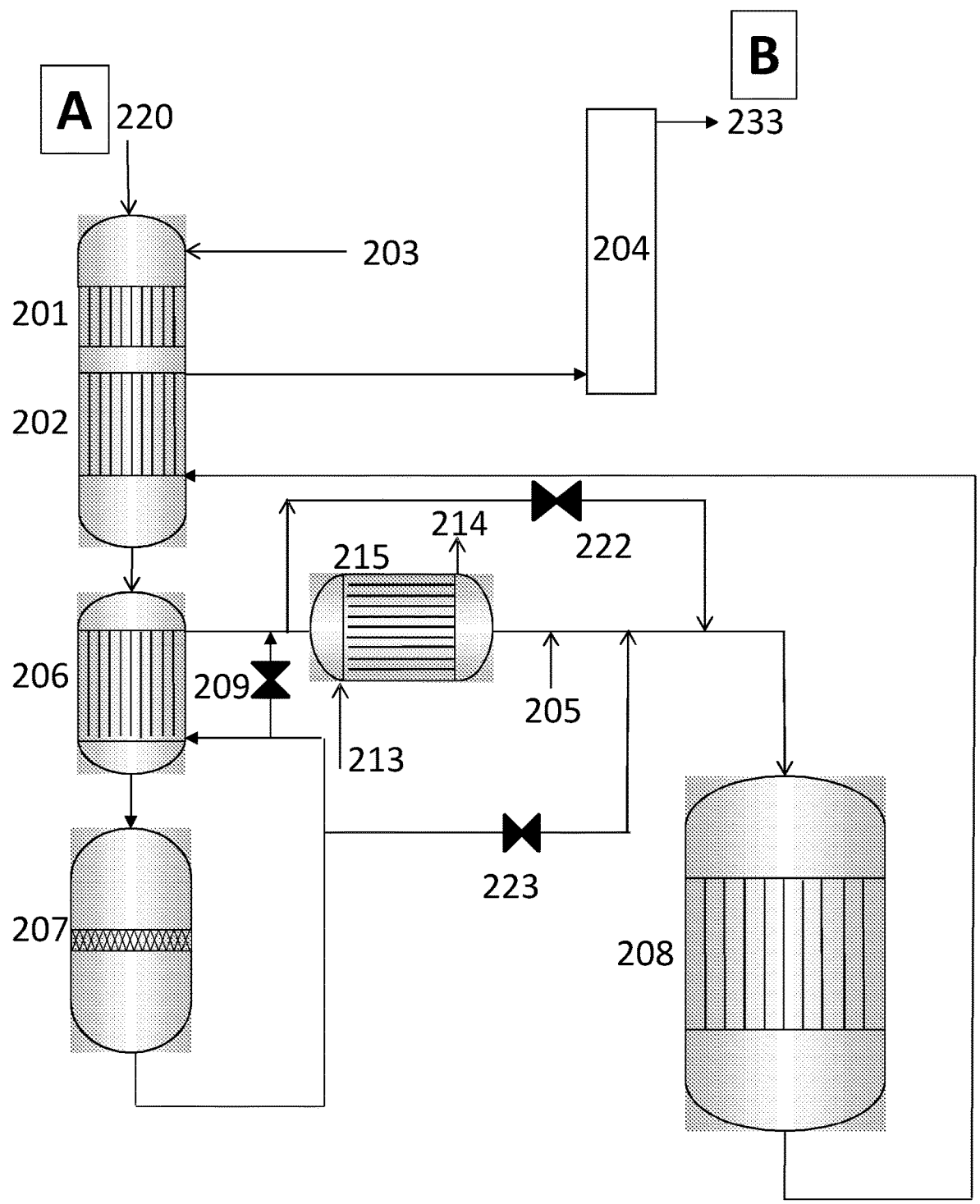
FIG. 8 is a schematic diagram of another part of the embodiment of FIG. 7.

In FIGS. 7 and 8, fresh air 625 entering the apparatus is fed to the compression side of a turbocharger 626. The air is compressed, mixed with recycled oxygen lean gas 233 leaving the absorber 204 and fed via recirculation blowers 632 to the inlet of pre-vaporiser 201 as recirculation stream 220. The apparatus in FIG. 8 is the apparatus of FIG. 3, with like parts identified by like numerals. It will be appreciated that the use of the apparatus of FIG. 3 is for example only and that any of the apparatus of FIG. 1, 2, 3, 4, 5, or 6 could be used with the apparatus of FIG. 7. In FIG. 8 the absorber 204 is depicted explicitly, with the output 233 from the absorber 204 being fed back, at point B, into the apparatus of FIG. 7. Part of the output 233 from the absorber 204 is fed to the Emission Control System (ECS) 630. The remainder is recycled and mixed with the compressed air coming from the turbocharger 626. In the ECS a catalytic incineration is used to remove hazardous wastes in the gas. In the example ECS 630 shown, the gas is first pre-heated using waste heat remaining downstream of the turbocharger 626 and then incinerated on a catalyst bed. However, any suitable ECS could be used and the pre-heat in the ECS could be achieved using other means. The, now hot, gases exiting the ECS 630 are fed to the turbine side 627 of the turbocharger 626 where they provide the energy to compress the incoming fresh air 625. The re-use of the energy in this way allows the fresh air 625 to be pressurised in an economically feasible way so that the resulting advantages of higher throughput are not cancelled out by the cost of achieving the pressurisation. Downstream of the turbine 627, the gas is optionally passed through a further energy recovery unit 631 before passing through the pre-heater of the ECS 630 and being vented to atmosphere 629. As stated above, the heat recovery downstream of the turbine may be carried out in alternative ways. For example, the energy recovery unit 631 may be omitted entirely, with all the energy recovery happening in the pre-heater of the ECS 630. The provision of the turbocharger 626 allows higher pressures to be obtained without incurring excessive cost. The pre-reactor 207 permits those high pressures to be used without excessively increasing the shut down time for catalyst replacement. Combining the turbocharger 626 with the pre-reactor 207 creates a particularly advantageous high pressure process.

It will be appreciated by persons skilled in the art that the above embodiments have been described by way of example only, and not in any limitative sense, and that various alterations and modifications are possible without departure from the scope of the invention as defined by the appended claims. For example, while the embodiments depicted here show separate pre-reactors and cooled tubular reactors, the pre-reactor section and the cooled tubular reactor section could be implemented as different sections in a single reactor vessel. For example the pre-reactor section and the tubular cooled reactor section could be arranged one above the other in a column. In some embodiments the feed stream may comprise methylal (dimethoxymethane) instead of methanol. Both methanol and methylal may be present in some embodiments. In some embodiments the pre-vaporiser may not be present and the vaporising and heating of the feed stream may be carried out in a single vaporiser, which may also act as a gas cooler as in the embodiments described, or in a different way.

The invention claimed is:

1. An apparatus for the production of formaldehyde, the apparatus comprising
a cooled tubular reactor section having a first inlet, a first outlet, and a plurality of tubes each having a first end in fluid communication with the first inlet and a second end in fluid communication with the first outlet, the plurality of tubes configured to contain, in use, a first catalyst for the production of formaldehyde by catalytic oxidative dehydrogenation,
a pre-reactor section having an inlet, and having an outlet in fluid communication with the first inlet of the cooled tubular reactor section, the pre-reactor section being configured to contain, in use, an adiabatic catalyst bed comprising a second catalyst for the production of formaldehyde by catalytic oxidative dehydrogenation, wherein the apparatus comprises a turbocharger to pressurize gas entering the apparatus and wherein the apparatus comprises an emissions control system for the combustion of waste gas from the production of the formaldehyde and the turbocharger is connected to the emissions control system such that the turbocharger can be powered by energy in the waste gas leaving the emissions control system.

2. The apparatus according to claim 1, wherein the cooled tubular reactor section further comprises a shell surrounding the plurality of tubes and having at least one second inlet and at least one second outlet for passing heat transfer fluid through the shell in use.

3. The apparatus according to claim 1, wherein the adiabatic catalyst bed is a packed bed of catalyst.

4. The apparatus according to claim 1, wherein the cross-sectional area of the catalyst bed of the pre-reactor section is in the range of 50% to 150% of the tubular cross-sectional area of the cooled tubular reactor section.

5. The apparatus according to claim 1, wherein the apparatus comprises a pre-reactor containing the pre-reactor section and a cooled tubular reactor containing the cooled tubular reactor section.

6. The apparatus according to claim 5, wherein the apparatus includes a heat exchanger connected to the inlet and the outlet of the pre-reactor section such that, in use, gas leaving the pre-reactor section is used to heat gas fed to the pre-reactor section.

7. The apparatus according to claim 6, wherein the apparatus further comprises a bypass valve connected between an input and an output of the heat exchanger such that some or all of the gas leaving the pre-reactor section can be diverted so as to bypass the heat exchanger.

8. The apparatus according to claim 6, wherein the apparatus comprises a steam generator connected to the outlet of the pre-reactor section to generate steam and cool gases leaving the pre-reactor section.

9. The apparatus according to claim 8, wherein the steam generator is connected to an output of the heat exchanger, so that a stream exiting the pre-reactor section flows, in use, to the steam generator via the heat exchanger.

10. The apparatus according to claim 8, wherein the steam generator is connected directly to the output of the pre-reactor section.

11. The apparatus according to claim 10, wherein an output of the steam generator is connected to the heat exchanger, so that a stream exiting the pre-reactor section flows, in use, to the heat exchanger via the steam generator.

12. The apparatus according to claim 10, wherein an output of the steam generator is connected directly to the cooled tubular reactor section.

13. The apparatus according to claim 1, wherein the apparatus comprises a further feed inlet connected to the first inlet of the cooled tubular reactor section such that, in use, methanol can be added between the outlet of the pre-reactor section and the first inlet of the cooled tubular reactor section.

14. The apparatus according to claim 13, wherein the apparatus comprises a heat exchanger connected to the first input and the first output of the cooled tubular reactor section such that, in use, heat can be exchanged between streams flowing to and from the cooled tubular reactor section.

15. The apparatus according to claim 14, wherein the further feed inlet is a further feed inlet into the heat exchanger.

16. A process for producing formaldehyde, the process comprising feeding a feed stream comprising methanol to a pre-reactor section operated adiabatically, at least partially converting methanol in the feed stream to formaldehyde in the pre-reactor section to produce a first product stream comprising formaldehyde, feeding the first product stream, optionally with addition of further methanol, to a cooled tubular reactor section, and at least partially converting methanol in the first product stream to formaldehyde in the cooled tubular reactor section to produce a second product stream comprising formaldehyde, wherein waste gas from the process is fed to an emissions control system for the combustion of the waste gas, and wherein a turbocharger is connected to the emissions control system and energy in the waste gas leaving the emissions control system powers the turbocharger to compress the feed stream.

17. The process according to claim 16, wherein the pre-reactor section comprises a catalyst bed and the cooled tubular reactor section comprises tubes containing catalyst and the process comprises operating the process for a period of time, and replacing the catalyst bed one or more times with a fresh catalyst bed during the period of time, wherein the catalyst in the tubes is not replaced during the period of time.

18. The process according to claim 16, wherein the process comprises operating the process, operating a bypass so that the pre-reactor section is isolated from the process and the feed stream is fed to the cooled tubular reactor section, replacing the catalyst in the pre-reactor section, and reversing the operation of the bypass so that the feed stream is once more fed to the pre-reactor section.

19. The process according to claim 16, wherein catalyst in the pre-reactor section is replaced more often than catalyst in the cooled tubular reactor section.

20. The process according to claim 16, wherein the process comprises adding methanol to the first product stream before feeding it to the cooled tubular reactor section.

* * * * *